United States Patent [19]

Pereira et al.

[11] Patent Number: 5,216,033
[45] Date of Patent: Jun. 1, 1993

[54] WATER-IN-OIL TRANSPARENT EMULSION FOR THE SKIN

[75] Inventors: Mavis C. Pereira, Lower Bebington, England; Udo Spiegel, Strahlauer Weg, Fed. Rep. of Germany

[73] Assignee: Chesebrough-Pond's USA Co., Division of Conopco, Inc., Greenwich, N.Y.

[21] Appl. No.: 546,156

[22] Filed: Jun. 28, 1990

[30] Foreign Application Priority Data

Jun. 29, 1989 [GB] United Kingdom ............... 8914905

[51] Int. Cl.⁵ .................. A61K 7/40; A61K 7/48; A61K 9/10; A61K 9/12
[52] U.S. Cl. .................... 514/844; 424/47; 424/59; 424/60; 424/63; 424/65; 424/66; 424/68; 424/69; 424/195.1; 514/847; 514/873; 514/880; 514/881; 514/937; 514/938; 514/944
[58] Field of Search ............... 424/65; 514/938, 847, 514/844

[56] References Cited

U.S. PATENT DOCUMENTS

| | | | |
|---|---|---|---|
| 4,105,782 | 8/1978 | Yu et al. | 424/DIG. 4 |
| 4,105,783 | 8/1978 | Yu et al. | 514/844 |
| 4,122,029 | 10/1978 | Gee et al. | 252/309 |
| 4,197,316 | 8/1980 | Yu et al. | 514/844 |
| 4,234,599 | 11/1980 | Van Scott et al. | 514/844 |
| 4,311,695 | 1/1982 | Starch | 424/78 |
| 4,363,815 | 12/1982 | Yu et al. | 514/844 |
| 4,424,341 | 1/1984 | Alderson et al. | 424/DIG. 5 |
| 4,720,353 | 1/1988 | Bell | 514/859 |
| 4,772,592 | 9/1988 | Benzoni | 514/859 |
| 5,015,469 | 5/1991 | Yoneyama et al. | 514/846 |

FOREIGN PATENT DOCUMENTS

| | | | |
|---|---|---|---|
| 0007785 | 2/1980 | European Pat. Off. | 514/938 |
| 0015030 | 9/1980 | European Pat. Off. | 514/844 |
| 0150914 | 8/1985 | European Pat. Off. | 514/938 |
| 0152953 | 8/1985 | European Pat. Off. | 424/DIG. 5 |
| 0160430 | 11/1985 | European Pat. Off. | 514/938 |
| 0251679 | 1/1988 | European Pat. Off. | 424/DIG. 5 |
| 0271925 | 6/1988 | European Pat. Off. | 514/938 |
| 0281394 | 9/1988 | European Pat. Off. | 514/938 |
| 0347198 | 12/1989 | European Pat. Off. | 424/70 |
| 2079300 | 1/1982 | United Kingdom | 514/938 |

OTHER PUBLICATIONS

Abstract for Japanese Patent 60:126209 (Lion).
Translation for German Patent 2110993.

*Primary Examiner*—Dale R. Ore
*Attorney, Agent, or Firm*—Milton L. Honig

[57] ABSTRACT

A water-in-silicone oil transparent emulsion is made from a volatile polydimethylsiloxane (1 to 50% by weight), a silicone surfactant (0.1 to 20% by weight), at least one polyhydric alcohol (1 to 50% by weight) and water.

The silicone surfactant comprises a polymer of dimethyl polysiloxane with polyoxyethylene and/or polyoxypropylene side chains having a molecular weight of from 10,000 to 50,000 and having the structure:

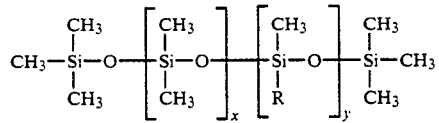

where R is $-H$ or $-[CH_2CH_2O]_a[CH_2CHO]_bH$
$\phantom{where R is -H or -[CH_2CH_2O]_a[CH_2CHO]_b}|$
$\phantom{where R is -H or -[CH_2CH_2O]_a[CH_2CHO]_bH\ }CH_3$ a having a value of from 9 to 115,
b having a value of from 0 to 50,
x having a value of from 133 to 673,
y having a value of from 25 to 0.25.

14 Claims, No Drawings

WATER-IN-OIL TRANSPARENT EMULSION FOR THE SKIN

FIELD OF INVENTION

The invention relates to a water-in-oil emulsion suitable for topical application to human skin and/or hair. More particularly, the invention is concerned with a water-in-silicone oil emulsion comprising a transparent gel matrix. This can be utilised to contain a skin and/or hair benefit substance such as a hydroxyalkanoic acid, in which case, the emulsion can be used to improve the quality, particularly the plasticity of skin to which it is applied, either as a beauty aid or in the treatment of damaged or diseased skin.

BACKGROUND TO INVENTION

A soft, supple and flexible skin has a marked cosmetic appeal and is an attribute of normal functioning epidermis.

As human skin ages with advancing years, the epidermis can become folded or ridged or furrowed to form wrinkles which signal the loss of youthful appearance and herald the transition to old age. This transition can occur prematurely with young people, especially those who expose themselves to excessive doses of sunlight. Also, the outer layer of the epidermis, that is the stratum corneum, can become dry and flaky following exposure to cold weather, or excessive contact with detergents or solvents which result in loss of skin moisture with the result that the skin loses its soft, supple and flexible characteristics.

Emollients such as fats, phospholipids and sterols have in the past been used to soften wrinkled or dry skin, but it is apparent that these emollients are only partially effective as a remedy for skin in poor condition.

Various other substances have been applied to skin and/or hair to confer various benefits.

Frequently an agent intended to confer a benefit for skin and/or hair constitutes only part of a product. Other material makes up the balance of the product and provides a carrier or vehicle for the active agent which is to be delivered to skin and/or hair. Products for application to skin and/or hair frequently take the form of emulsions which can be oil-in-water or water-in-oil emulsions. There have been various proposals of water-in-silicone oil emulsions.

US-A-4122029 (Dow Corning) teaches the formation of such emulsions with incorporation of a non-silicon emulsifier. US-A-4311695 (Dow Corning) teaches formation of such emulsions with a water and alcohol solution as the disperse phase and with an oil or fat included in the continuous phase. The suggested alcohols include ethanol, isopropanol, propylene glycol and glycerol but not polyhydric alcohols with 4 to 8 carbon atoms.

EP-A-271925 (Dow Corning) discloses water-in-silicone oil emulsions which are used as the base for cosmetic products such as eye shadow which include coloured pigment. EP-A-281394 (Richardson-Vicks) describes water-in-oil emulsions where the disperse phase is itself an oil-in-water emulsion. GB-A-2206048 (Boots) discloses water in silicone oil emulsions which spontaneously separate on standing but can be re-emulsified by shaking.

The documents referred to above use a volatile methyl siloxane fluid and a polydiorganosiloxane polyoxyalkylene copolymer.

It has also been proposed in EP-A-0 150 914 (Unilever) to provide a water-in-silicone oil emulsion containing an alkyl lactate and a silicone oil ingredient comprising a dispersion in a volatile siloxane of a polymer of dimethyl polysiloxane with polyoxyethylene and/or polyoxypropylene side chains, together with a nonionic liquid emulsifier having an HLB value of from 1 to 7, and a lower alkanol.

GB-A-2079300 (General Electric Company) discloses silicone oil-in-water emulsions containing non-silicon emulsifiers which are rendered transparent by incorporation of polyols.

The use of 2-hydroxyalkanoic acids for enhancing the quality of human skin following topical application thereto has already been described.

Thus, EP-A 0 007 785 (Unilever) discloses skin treatment compositions incorporating α-hydroxycaproic acid or α-hydroxycaprylic or mixtures thereof, the compositions having a pH value of less than 7, usually from pH values of from 2 to 4.

It is also proposed in US-A-4 105 782 (Yu & Van Scott) to use amines or ammonium salts of α-hydroxyacids in the treatment of acne or dandruff and, in the Yu & Van Scott patents U.S. Pat. No. 4,105,783 and U.S. Pat. No. 4,197,316, to use such compounds in the treatment of dry skin. U.S. Pat. No. 4,234,599 (Yu & Van Scott) discloses the use of α-hydroxyacids, and their esters or amine salts in the treatment of keratoses. In U.S. Pat. No. 4,363,815 (Yu & Van Scott) it is proposed to use α-hydroxyacids or β-hydroxyacids or keto acids or their derivatives, in a composition for treating skin conditions.

According to GB 1 471 679, (Avon) it is known to use alkali metal salts of $C_2$-$C_5$ α-hydroxycarboxylic acids in moisturising compositions.

In DE 2 110 993, (Henkel) there are disclosed alkali metal salts $C_4$-$C_{10}$ α-hydroxycarboxylic acids, and the sodium salt of α-hydroxycaprylic acid is mentioned.

SUMMARY OF THE INVENTION

We have now found that attractive transparent water-in-silicone oil emulsions possessing excellent storage stability can be formed using silicone oils which contain volatile methyl siloxane fluid and certain polydiorganosiloxane polyoxyalkylene copolymers. These emulsions can have gel like properties. To achieve transparency these emulsions also contain a polyhydric alcohol acting as a transparency structurant to provide a transparent emulsion. The emulsions can display very considerable stability even at elevated or sub-freezing temperatures. They have an attractive feel when applied to the skin. The transparent appearance and superior skin feel provide considerable consumer appeal.

The emulsion can provide a matrix which acts as a vehicle for other skin and/or hair benefit substances. In particular, we have found that these emulsions have superior properties for delivery to the skin of a 2-hydroxalkanoic acid. Attempts to provide other product forms, as carriers for such acids, in particular oil-in-water emulsions, tended to give products with poor feel when applied to the skin, for instance unduly greasy, sticky or both. We have found that when 2-hydroxyalkanoic acids are incorporated into emulsions according to the present invention these emulsions retain their properties of pleasant feel when applied to the skin and good storage stability.

DEFINITION OF THE INVENTION

Accordingly, the invention provides a water-in-silicone oil transparent emulsion, suitable for topical application to mammalian skin or hair, which comprises, in addition to water;

i. from 1 to 50% by weight of a volatile polydimethylsiloxane, ii. from 0.1 to 20% by weight of a silicone surfactant comprising a polymer of dimethyl polysiloxane with polyoxyethylene and/or polyoxypropylene side chains having a molecular weight of from 10,000 to 50,000 and having the structure:

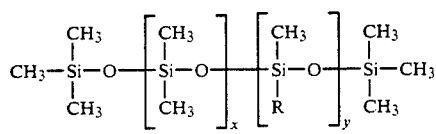

where R is $-H$ or $-[CH_2CH_2O]_a[CH_2CHO]_bH$
$\phantom{where R is -H or -[CH_2CH_2O]_a[CH_2CH}|$
$\phantom{where R is -H or -[CH_2CH_2O]_a[CH_2CH}CH_3$ a having a value of from 9 to 115,
b having a value of from 0 to 50,
x having a value of from 133 to 673,
y having a value of from 25 to 0.25, and iii. from 1 to 50% by weight of at least one polyhydric alcohol as transparency structurant.

DISCLOSURE OF THE INVENTION

The emulsion of the invention is a water-in-silicone oil emulsion, which is particularly suitable for topical application to mammalian skin or hair, particularly that of the human subject. The emulsion is unusual in as much as it is transparent, this being due to the careful choice of both a silicone emulsifier and a special polyhydric alcohol, which acts as a transparency structurant.

The emulsion can provide a transparent matrix preferably with gel-like properties as a vehicle for skin and/or hair benefit substances which can thereby be applied, with much greater ease and control to the skin or hair at an appropriate concentration suited to their intended benefit. The gel matrix itself also has great consumer appeal, particularly when applied to the human skin or hair, in that transparency has a connotation of being natural and pure, and that the application of the gel to the skin in particular is pleasurable.

The Polydimethylsiloxane

The emulsion of the invention comprises a volatile polydimethylsiloxane such as polydimethylcyclosiloxane having a viscosity of less than 5 mm²s⁻¹, examples of which are DOW CORNING 344 Fluid (tetramer) and DOW CORNING 345 Fluid (pentamer), and volatile hexamethyldisiloxane having a viscosity of not more than 0.65 mm²s⁻¹, for example DOW CORNING 200 Fluid (0.65 mm²s⁻¹).

The preferred volatile siloxane is polydimethylcyclosiloxane (pentamer).

The emulsion will normally comprise from 1 to 50%, preferably from 5 to 20% by weight of the volatile siloxane.

Silicone Surfactant

The emulsion of the invention also comprises a high molecular weight silicone surfactant which acts as an emulsifier.

The silicone surfactant is a high molecular weight polymer of dimethyl polysiloxane with polyoxyethylene and/or polyoxypropylene side chains having a molecular weight of from 10,000 to 50,000 and having the structure:

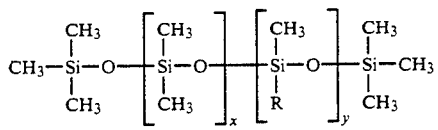

where R is $-H$ or $-[CH_2CH_2O]_a[CH_2CHO]_bH$
$\phantom{where R is -H or -[CH_2CH_2O]_a[CH_2CH}|$
$\phantom{where R is -H or -[CH_2CH_2O]_a[CH_2CH}CH_3$ a has a value of from 9 to 115,
b has a value of from 0 to 50,
x has a value of from 133 to 673,
y has a value of from 25 to 0.25.

Preferably, the dimethyl polysiloxane polymer is one in which:
a has a value of from 10 to 114
b has a value of from 0 to 49
x has a value of from 388 to 402
y has a value of from 15 to 0.75
the group R having a molecular weight of from 1000 to 5000.

A particularly preferred dimethyl polysiloxane polymer is one in which:
a has the value 14
b has the value 13
x has the value 249
y has the value 1.25

The dimethyl polysiloxane polymer is conveniently provided as a dispersion in a volatile siloxane, the dispersion comprising, for example, from 1 to 20% by volume of the polymer and from 80 to 99% by volume of the volatile siloxane. Ideally, the dispersion consists of a 10% by volume of the polymer dispersed in the volatile siloxane.

Examples of the volatile siloxanes in which the polysiloxane polymer can be dispersed include those given above.

A particularly preferred silicone surfactant is cyclomethicone and dimethicone copolyol such as DC 3225C Formulation Aid available from DOW CORNING.

The emulsion according to the invention will normally comprise from 0.1 to 20%, preferably from 0.5 to 15% by weight of the silicone surfactant. This may be the only emulsifier present.

NON-VOLATILE SILOXANE

The emulsion can also, optionally, comprise a non-volatile siloxane such as a polydimethylsiloxane having a viscosity in excess of 5 mm²s⁻¹, for example, from 50 to 1000 mm²s⁻¹, for example DOW CORNING 200 Fluids (standard viscosities 50-1000 mm²s⁻¹).

The Transparency Structurant

The emulsion of the invention also comprises a transparency structurant which is at least one polyhydric alcohol. The polyhydric alcohol may have 3 or 4 to 8 carbon atoms, but polyalkylene glycols are also suitable.

Examples of transparency structurants include sugar alcohols having the structure:

$$HOCH_2(CHOH)_nCH_2OH$$

where n is an integer of from 2 to 6. Particular examples of sugar alcohols include:

Tetritols, such as erythritol, Pentitols, such as ribitol, xylitol, D-arabitol, Hexitols, such as allitol, sorbitol (also known as D-glucitol), L-glucitol, D-mannitol, L-talitol, D-iditol, Heptitols, such as glyceroglucoheptitol, Octitol, such as D-erythro-D-galactooctitol.

The preferred polyhydric alcohol for inclusion in the emulsion of the invention is sorbitol, which is normally available as a 70% by weight solution in water.

The emulsion will normally comprise from 1 to 50%, preferably from 2 to 40% by weight of the transparency structurant. The amount of this material should be chosen, within the quoted ranges, so that transparency is achieved. The amount needed will depend on the other constituents of the emulsion and the amounts of them. The level of transparency structurant(s) required to achieve transparency can be determined by an experimental procedure. In this procedure the oil and water phases are made up separately and their refractive indices are measured. The formulations of the phases are then modified until the refractive indices of the two phases are the same. The principal adjustment is by changing the percentage of transparency structurant in the aqueous phase.

Water

The emulsion comprises water, or an aqueous solution, as the disperse phase. The amount of water may lie in the range not exceeding 50% by weight although higher percentages are not ruled out and will generally exceed 25% by weight.

SKIN AND/OR HAIR BENEFITS SUBSTANCES

The water-in-oil transparent emulsion according to the invention can provide a matrix to serve as a vehicle in which a skin and/or hair benefit substance can be dissolved, dispersed or suspended. Examples of skin and/or hair benefit substances include:

i. 2-Hydroxyalkanoic acids having from 3 to 28 carbon atoms, preferred examples of which include 2-hydroxypropanoic acid, 2-hydroxhexanoic acid and 2-hydroxyoctanoic acid.

ii. Acid-soap complexes of 2-hydroxyalkanoic acids having from 6 to 28 carbon atoms, preferred examples of which have an elemental analysis of:

$$(C_mH_{2m-1}O_3)(C_mH_{2n-1}O_3)M \quad (1)$$

where m and n have the same or different values, and each is an integer of from 6 to 28, and M is a cation. The cation M is a monovalent ion such as potassium, sodium or ammonium. A particularly preferred example of the acid-soap complex is that derived from two molecules of 2-hydroxyoctanoic acid which has the empirical formula $C_{16}H_{31}O_6Na$.

iii. Antiperspirant agents, such as astringent metal salts, for example aluminium chloride, aluminium chlorohydrate, activated aluminium chlorohydrate and zirconium salts.

iv. Sunscreen agents, such as p-aminobenzoic acid, ethylhexyl p-methoxycinnamate and 2-ethoxyethyl-p-methoxycinnamate.

v. Natural moisturising factor substances such as esters of pyroglutamic acid, such as pyroglutamic acid ethyl ester and ethyl-2-[pyroglutamoyloxy]-n-propionate.

vi. Hair growth promoters such as glucarolactams, glucarolactones and diacylglycerols.

The emulsion of the invention can comprise from 0.01 to 50% by weight of any skin and/or hair benefit substance, such as those exemplified above.

OTHER INGREDIENTS

Cosmetically Acceptable Vehicle

The emulsion of the invention can optionally comprise -some other cosmetically acceptable vehicle, in addition to water, to act as a dilutant, dispersant or carrier for other materials present in the emulsion, so as to facilitate their distribution when the emulsion is applied to the skin and/or hair.

Vehicles other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, glyceryl monostearate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, evening primrose oil, soybean oil, sunflower seed oil, avocado oil, olive oil, sesame seed oil, coconut oil, arachis oil, castor oil, acetylated lanolin alcohols, petroleum jelly, mineral oil, butyl myristate, isostearic acid, palmitatic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, monoethyl ether, diethylene glycol monobutyl ether, diethylene glycol monoethyl ether, dimethyl sulphoxide, dimethyl formamide, tetrahydrofuran;

Powders, such as chalk, talc, fullers earth, kaolin, starch, gums, colloidal silica, sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate, titanium dioxide, titanium dioxide-coated mica.

The cosmetically acceptable vehicle, when present, will usually form from 10 to 99.9%, preferably from 50 to 99% by weight of the emulsion, and can, in the absence of other cosmetic adjuncts, form the balance of the emulsion.

Cosmetic Adjuncts

Examples of conventional adjuncts which can optionally be employed include preservatives, such as parahydroxy benzoate esters; antioxidants, such as butyl hydroxy toluene; humectants, such as propanediol, butane-1,3-diol, glycerol, 2-pyrrolidone-5-carboxylate, dibutylphthalate, gelatin, polyethylene glycol, preferably PEG 200-600; stabilisers, such as sodium chloride or ammonium chloride; buffer system, such as lactic acid together with a base such as triethanolamine or sodium hydroxide; waxes, such as beeswax, ozokerite wax, paraffin wax; plant extracts, such as Aloe vera, cornflower, witch hazel, elderflower, cucumber; amino acids such as L-proline; thickeners; activity enhancers; colourants; perfumes; emulsifiers; and sunscreens.

Cosmetics adjuncts can form up to 50% by weight of the emulsion and can conveniently form the balance of the emulsion.

It is to be understood that whereas the gel emulsion according to the invention is transparent, transparency can be lost or impaired by the inclusion of certain skin and/or hair benefit substances or certain of the vehicles or cosmetic adjuncts given herein.

pH

The aqueous phase of the emulsion according to the invention should preferably have a pH value of from 3.5 to <7.

PROCESSING FOR PREPARING THE EMULSION

The invention also provides a process for the preparation of an emulsion for topical application to skin and/or hair which comprises the step of incorporating into the emulsion a volatile polydimethylsiloxane, a silicone surfactant and a transparency structurant as herein defined.

PRODUCT FORM AND PACKAGING

The topical skin and/or hair treatment emulsion of the invention can be formulated as a gel which is suitable for dispensing from a roll-ball applicator or a propellant-driven aerosol device or a container fitted with a pump suitable for finger operation. Alternatively, the emulsion can simply be stored in a non-deformable bottle or squeeze container, such as a tube or a lidded jar.

The invention accordingly also provides a closed container containing a cosmetically acceptable emulsion as herein defined.

EXAMPLES

The invention is further illustrated by the following examples.

EXAMPLE 1

This example illustrates a transparent gel which is suitable for topical application to human skin. The gel had the following formulation:

| Ingredient | % w/w |
| --- | --- |
| Volatile siloxane (DC 345 Fluid) | 10 |
| Silicone surfactant (DC 3225C) | 10 |
| 2-hydroxyoctanoic acid | 1 |
| Sorbitol (70% aqueous solution) | 10 |
| Polyethyleneglycol 400 | 9 |
| Butane-1,3-diol | 10 |
| Preservative | qs |
| Buffer (aqueous phase to pH 4.5) | qs |
| Water | to 100 |

Samples of the gel of this example were tested for freeze/thaw stability by cycling from ambient temperature (20° C.) to −22° C. and back again. After four such cycles the emulsion was observed still to be stable, remaining in the state in which it was originally prepared.

With regard to elevated temperature storage, samples of this gel formulation remained stable for nine months at 45° C. (three months storage at this temperature is the industry standard requirement). Further samples remained stable for the same period at 35° C. Samples also remained stable when stored for a year at ambient temperature.

EXAMPLE 2

This example illustrates a transparent gel matrix, containing suspended therein fraction of a percent of titanium dioxide coated mica to provide a coloured translucent iridescent gel which is suitable for topical application to human skin. The gel had the following formulation:

| Ingredient | % w/w |
| --- | --- |
| Volatile siloxane (DC 345 Fluid) | 13 |
| Silicone surfactant (DC 3225C) | 8 |
| 2-hydroxyoctanoic acid | 1 |
| Sorbitol (70% aqueous solution) | 10 |
| Ethanol | 8 |
| Polyethyleneglycol 400 | 7 |
| Butane-1,3-glycol | 8 |
| Preservative | qs |
| Titanium dioxide coated mica | qs |
| Colourant | qs |
| Buffer (aqueous phase to pH 4.5 to 5) | qs |
| Water | to 100 |

Viscosity: 70,000 to 80,000 m Pa.s at 30° C.

Samples stored for 3 months at 37° C., and other samples stored for 3 months at 45° C. remained entirely stable.

We claim:

1. A water-in-silicone oil transparent emulsion, suitable for topical application to mammalian skin which comprises, in addition to water;
   i. from 1 to 50% by weight of a volatile polydimethylsiloxane;
   ii. from 0.1 to 20% by weight of a silicone surfactant ingredient comprising a polymer of dimethyl polysiloxane with polyoxyethylene and/or polyoxypropylene side chains having a molecular weight of from 10,000 to 50,000 and having the structure:

$$CH_3-\underset{\underset{CH_3}{|}}{\overset{\overset{CH_3}{|}}{Si}}-O\left[\underset{\underset{CH_3}{|}}{\overset{\overset{CH_3}{|}}{Si}}-O\right]_x\left[\underset{\underset{R}{|}}{\overset{\overset{CH_3}{|}}{Si}}-O\right]_y\underset{\underset{CH_3}{|}}{\overset{\overset{CH_3}{|}}{Si}}-CH_3$$

where R is $-H$ or $-[CH_2CH_2O]_a[CH_2\underset{\underset{CH_3}{|}}{CH}O]_bH$ a having a value of from 9 to 115, b having a value of from 0 to 50, x having a value of from 133 to 673, y having a value of from 25 to 0.25, and iii. from 1 to 50% by weight of a transparency structurant which is at least one polyhydric alcohol.

2. An emulsion according to claim 1, in which the volatile polydimethylsiloxane is polydimethylcyclosiloxane (tetramer).

3. An emulsion according to claim 1 in which the volatile polydimethysiloxane is polydimethylcyclosiloxane (pentamer).

4. An emulsion according to claim 1, in which the silicone, surfactant is one in which:

a has a value of from 10 to 114 b has a value of from 0 to 49 x has a value of from 388 to 402 and y has a value of from 15 to 0.75;

the group R having a molecular weight of from 1000 to 5000.

5. An emulsion according to claim 1, in which the silicone surfactant is one in which:

a has the value 14 b has the value 13 x has the value 249, and y has the value 1.25

6. An emulsion according to claim 1 in which the polyhydric alcohol is chosen from those having 3 to 8 carbon atoms.

7. An emulsion according to claim 6 in which the polyhydric alcohol is an alcohol having from 4 to 6 carbon atoms.

8. An emulsion according to claim 7, in which the polyhydric alcohol is sorbitol.

9. An emulsion according to claim 1 in which the polyhydric alcohol is polyethylene glycol.

10. An emulsion according to claim 1, which further comprises, as a skin beneficial substance, a 2-hydroxyalkanoic acid having from 3 to 28 carbon atoms.

11. An emulsion according to claim 10, in which the 2-hydroxyalkanoic acid is 2-hydroxyoctanoic acid.

12. An emulsion according to claim 1, which further comprises an acid-soap complex of a 2-hydroxyalkanoic acid having the structure (1):

$$(C_mH_{2m-1}O_3)(C_nH_{2n-1}O_3) M$$

where m and n have the same or different values, and each is an integer of from 6 to 28, and where M is a monovalent cation ion.

13. An emulsion according to claim 12, in which the acid-soap complex has the empirical formula:

$$C_{16}H_{31}O_6Na.$$

14. An emulsion according to claim 1, which further comprises a non-volatile siloxane.

* * * * *